US012582479B2

(12) United States Patent
Audigier et al.

(10) Patent No.: US 12,582,479 B2
(45) Date of Patent: Mar. 24, 2026

(54) METHOD AND SYSTEM FOR AUTOMATIC PLANNING OF A MINIMALLY INVASIVE THERMAL ABLATION AND METHOD FOR TRAINING A NEURAL NETWORK

(71) Applicant: Siemens Healthcare GmbH, Erlangen (DE)

(72) Inventors: Chloe Audigier, Bern (CH); Tommaso Mansi, Plainsboro, NJ (US)

(73) Assignee: Siemens Healthineers AG, Erlangen (DE)

( * ) Notice: Subject to any disclaimer, the term of this patent is extended or adjusted under 35 U.S.C. 154(b) by 237 days.

(21) Appl. No.: 18/295,887

(22) Filed: Apr. 5, 2023

(65) Prior Publication Data

US 2023/0310083 A1 Oct. 5, 2023

(30) Foreign Application Priority Data

Apr. 5, 2022 (EP) .................................... 22166759

(51) Int. Cl.
| | |
|---|---|
| *A61B 34/10* | (2016.01) |
| *A61B 90/00* | (2016.01) |
| A61B 18/00 | (2006.01) |

(52) U.S. Cl.
CPC .............. *A61B 34/10* (2016.02); *A61B 90/36* (2016.02); *A61B 2018/00577* (2013.01); *A61B 2034/107* (2016.02); *A61B 2090/364* (2016.02)

(58) Field of Classification Search
CPC ................... A61B 34/10; A61B 90/36; A61B 2018/00577; A61B 2034/107;
(Continued)

(56) References Cited

U.S. PATENT DOCUMENTS

| | | |
|---|---|---|
| 2019/0008591 A1 | 1/2019 | Desai et al. |
| 2022/0117668 A1 | 4/2022 | Quin et al. |

FOREIGN PATENT DOCUMENTS

| | | |
|---|---|---|
| WO | WO 2020143715 A1 | 7/2020 |
| WO | WO 2021029973 A1 | 2/2021 |

OTHER PUBLICATIONS

Weihusen, A. et. al., "Towards a workflow-oriented software assistance for the radiofrequency ablation", Informatik für Menschen, Band 1, 2006; 2006.
(Continued)

*Primary Examiner* — Michael J Carey
*Assistant Examiner* — Zainab Mohammed Aldarraji
(74) *Attorney, Agent, or Firm* — Laurence A. Greenberg; Werner H. Stemer; Ralph E. Locher

(57) ABSTRACT

A computer-implemented method for planning a thermal ablation of a target object within a biological body includes acquiring an object image within the body, determining an object position within the body from the image, determining external body surface position relative to the object position from the image, acquiring, for an initial set of ablation needles those of types for the ablation, and for each type, a set of characterizing features common to all needles of a same type, including a fixed and/or variable parameter. A neural ordinary differential equation algorithm receives a characterizing feature, external surface position, object position, algorithm for outputting an ablation plan, including a final set of needles for ablating the object, and for each needle of the final set, type, trajectory from the external surface, and optionally, a variable parameter value. The plan is provided through an interface to guide a clinician for object ablation.

12 Claims, 3 Drawing Sheets

(58) Field of Classification Search
CPC ... A61B 2090/364; A61B 34/25; A61B 6/032;
A61B 6/5217; A61B 18/1477; A61B
2018/0016; A61B 2018/1467; A61B
2018/1475; A61B 2034/254; A61B
2090/365; A61B 2090/3762; A61B
2576/00; A61B 2034/104; A61B 18/12;
A61B 18/1402; A61B 34/20; A61B
2018/00529; A61B 2018/00595; A61B
2018/1425; A61B 2034/108; A61B
2034/2065; G06N 3/045; G06N 3/09;
G06N 3/04; G06N 3/08
See application file for complete search history.

(56) References Cited

OTHER PUBLICATIONS

Solbiati, M. et al., "A novel software platform for volumetric assessment of ablation completeness", International Journal of Hyperthermia, 36(1), 337-343, 2019; 2019.

Yoon et al., "Prediction of Local Tumor Progression after Radiofrequency Ablation (RFA) of Hepatocellular Carcinoma by Assessment of Ablative Margin Using Pre-RFA MRI and Post-RFA CT Registration", Korean Journal of Radiology, 2018, pp. 1053-1065.; 2018.

Bale et al.: "Stereotaxy: Breaking the limits of current radiofrequency ablation techniques", Euro J. Radiol, 75 (2010), p. 32-36; 2010.

Seitel et al., "Computer-assisted trajectory planning for percutaneous needle insertions", Medical Physics, 2011, pp. 3246-3259.; 2011.

Cascination, Computer-assisted and image-guided surgery, https://www.cascination.com/, Stand: Feb. 18, 2020.

Laimer et al., "Minimal ablative margin (MAM) assessment with image fusion: an independent predictor for local tumor progression in hepatocellular carcinoma after stereotactic radiofrequency ablation", European Radiology, 2020, pp. 2463-2472; 2020.

Van Strijen, "Live 3D needle guidance with XperGuide", Philips, https://philipsproductcontent.blob.core.windows.net/assets/20170523/ec28809e9c0d43d6a602a77c0158e4c8.pdf, 2008, 4 pgs.; 2008.

Razzaque, Sharif et al.: "Navigation for Image-Guided Ablation: Exploring Its Unique Application and Associated Challenges"; Medtronic; 2017; https://www.medtronic.com/content/dam/covidien/library/us/en/product/ablation-systems/emprint-sx-navigation-forimage-guided-ablation-white-paper.pdf.

Bale, R. et al., "Stereotactic Radiofrequency Ablation of Hepatocellular Carcinoma: a Histopathological Study in Explanted Livers", Hepatology, 70(3), 840-850, 2019.

Zhang, R. et al., "Computer-assisted needle trajectory planning and mathematical modeling for liver tumor thermal ablation: A review", Mathematical Biosciences and Engineering, 16(5), pp. 4846-4872, 2019.

Perkel K.M. et al.:"Julia: come for the syntax, stay for the speed." Nature 572.7768 (2019): 141-143.

Kim, K. W. et al., "Safety Margin Assessment After Radiofrequency Ablation of the Liver Using Registration of Preprocedure and Postprocedure CT Images", American Journal of Roentgenology, 196(5), W565-W572, 2011; 2011.

Bale, R. et al., "Percutaneous stereotactic radiofrequency ablation of colorectal liver metastases", Eur Radiol. 22(4), pp. 930-937, published online Nov. 10, 2011.

Liang L. et al: "Development of a Multi-objective Optimized Planning Method for Microwave Liver Tumor Ablation", In International Conference on Medical Image Computing and Computer-Assisted Intervention, MICCAI 2019 (pp. 110-118), Springer.

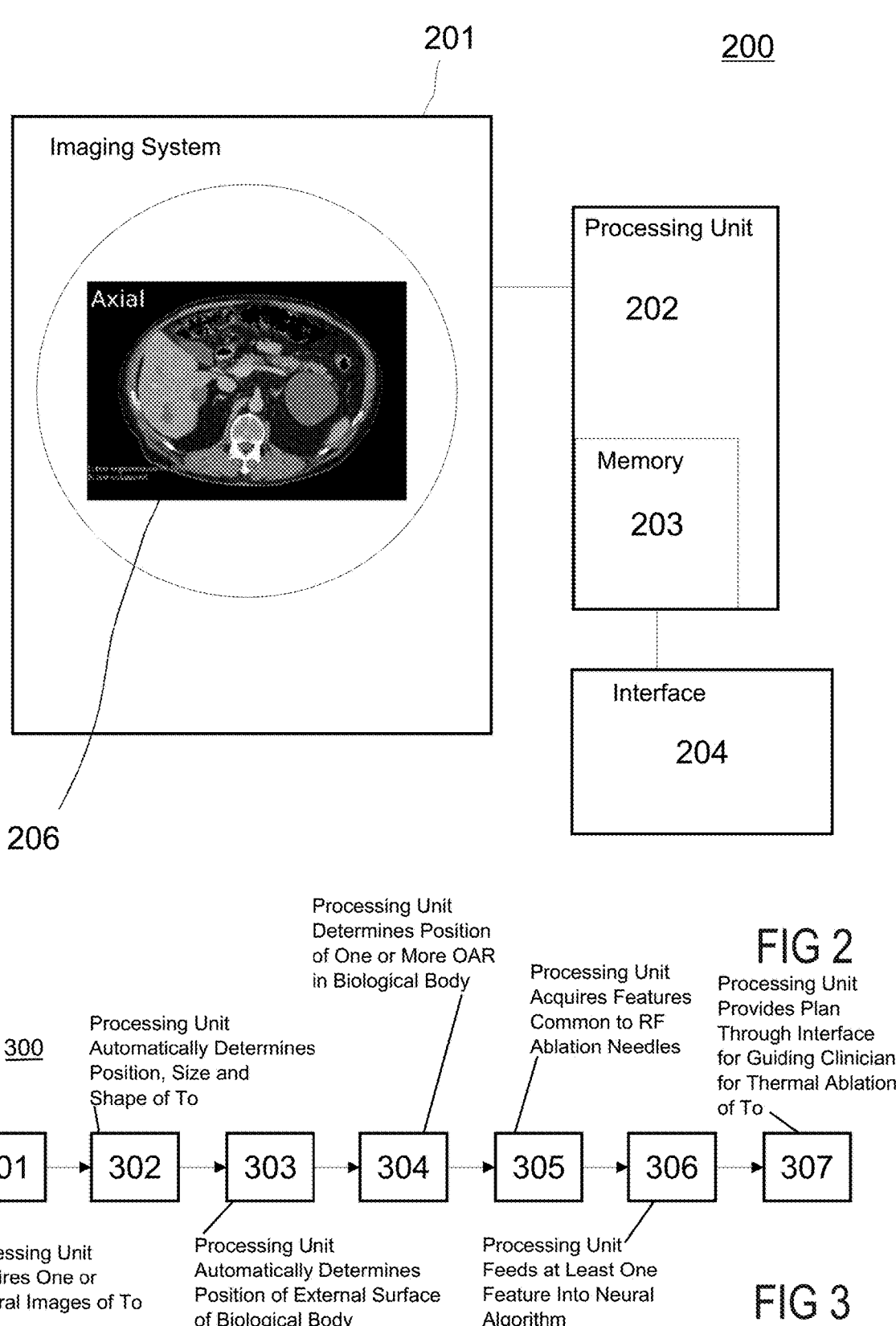

201

200

Imaging System

Axial

Processing Unit

202

Memory

203

Interface

Processing Unit Acquires One or Several Images of To

Processing Unit Automatically Determines Position, Size and Shape of To

Processing Unit Automatically Determines Position of External Surface of Biological Body Processing Unit Determines Position of One or More OAR in Biological Body Processing Unit Acquires Features Common to RF Ablation Needles Processing Unit Feeds at Least One Feature Into Neural Algorithm Processing Unit Provides Plan Through Interface for Guiding Clinician for Thermal Ablation of To

FIG 3

METHOD AND SYSTEM FOR AUTOMATIC PLANNING OF A MINIMALLY INVASIVE THERMAL ABLATION AND METHOD FOR TRAINING A NEURAL NETWORK

CROSS-REFERENCE TO RELATED APPLICATION

This application claims the priority, under 35 U.S.C. § 119, of European Patent Application EP 22166759.5, filed Apr. 5, 2022; the prior application is herewith incorporated by reference in its entirety.

FIELD AND BACKGROUND OF THE INVENTION

The present invention relates, in general, to thermal ablation techniques, and in particular radiofrequency (RF) thermal ablation techniques.

Thermal ablation is a technique enabling the destruction of tissue by extreme hyperthermia. It is a minimally invasive alternative to resection and transplantation in the treatment of primary and metastatic liver tumors. Today, the current conventional workflow for thermal ablation includes four main steps: (i) a planning phase, (ii) an intervention phase which includes targeting the tumor as defined in the planning phase, followed by (iii) the ablation itself and finally (iv) a validation phase where the generated ablation zone is compared to the tumor. The present invention focuses on the planning phase.

While the present invention will be mainly described in connection with the example of RF thermal ablation, it may apply to other thermal ablation techniques (e.g. microwave, laser, or cryoablation, etc.).

RF thermal ablation, also simply called "RFA", has shown excellent results for the treatment of rather small tumors (diameter <3 cm). However it still suffers from high recurrence rate for large (diameter >3-5 cm), irregularly shaped, or subcapsular lesions as well as lesions close to major vessels. For instance, a minimum ablation margin of 5 mm around the tumor has been shown to be the threshold that predicts local recurrence after ablation [1]. Additionally, incomplete ablation (i.e. viable tumor left unablated) is linked to an increased aggressivity of the tumor. And that is independent of the tumor size. A recent study shows good results even in lesions of diameter larger than 3 cm when using a stereotactic approach with several needles (up to 17) inserted to create overlapping ablation areas [2]. Indeed, the RFA antennas generally have a short diameter (the ablation area is usually ellipsoidal) of 2-3 cm, meaning that if a 5 mm margin around the tumor needs to be achieved, the maximum size of tumor addressable with a single needle—in optimal conditions—is 2 cm. Optimal conditions in the liver—a tumor that is not close to any major vessel—are scarce, and the median size of the tumors treated with ablation in most series is 3 cm [3,4]. Therefore, the tumors that can be safely treated with a single RFA antenna are the exception rather than the rule. In any case, when ablation can be performed with a single antenna, planning the insertion path and targeting the tumor, require only seeing it and means to direct a needle; ultrasound is often enough for that task. Tumors larger than what can be treated with a single antenna, require the creation of multiple overlapping ablation areas that cover the whole tumor and leave a sufficient margin.

However, the planning of multiple needles to create those overlapping ablation areas (between ablation needles, and with the same needle by pulling it back) is a very challenging spatial problem for most people. Today, it is mainly performed manually: the clinician plans the intervention by looking at pre-operative CT or MR images of the patient in 2D views and is then required to mentally map the developed plan onto the patient during intervention. That planning can take hours in complex cases. Since the thermal ablation planning relies on the personal experience of physicians [5,6], it is a time-consuming and operator-dependent task. That leads to the fact that the optimal plan is not guaranteed and therefore to a high possibility of incomplete tumor ablation and/or unnecessary excessive ablation of normal tissue.

Additionally, in order to deliver a useful plan, namely a plan that can be used during the intervention, navigation tools are required in such a way that the clinicians are able to position the needles in the precise locations that were defined during the planning phase. Navigation systems are often stand-alone systems, the user is required to transfer the imaging dataset to the workstation and plan the procedure there. Navigation tools also require absolute control on the position of the liver, so the best approach is to have the patient under general anesthesia and full muscular relaxation. That means that if intraoperative imaging is used to plan the ablation—as it should—the patient might stay under general anesthesia and fixed to the table for prolonged periods where the only action is planning the needle trajectories.

All those limitations lead to a suboptimal planning approach that can be very constraining for a successful ablation and can result in prolonged procedural time and increased risk.

Finally, the validation of the ablation margin in those cases is usually done days after doing a CT scan and comparing side to side the diagnostic CT and the post-ablation CT. That is frequently associated with sub-optimal ablation margins and explains why the local recurrences after ablation are relatively high—and highly inconsistent among different centers—. Studies which assessed it in detail, show between 65% and 75% of sub-optimal ablation margins. In the best case, the patient is rescheduled to a second ablation session to complete the ablation some weeks after—with the risk of the tumor biology already being changed. In the worst case, the suboptimal margin is not detected, and the patient has an "early recurrence," which is just the result of incomplete treatment.

SUMMARY OF THE INVENTION

It is accordingly an object of the invention to provide a method and a system for automatic planning of a minimally invasive thermal ablation and a method for training a neural network, which overcome the hereinafore-mentioned disadvantages of the heretofore-known methods and systems of this general type, which are capable of decreasing the complexity and duration of the thermal ablation planning, which enable a repeatable, operator independent, and reliable standardized planning, which ensure a minimum of 5 mm ablation margin, and which are based on the same pre-operative information that will be used for and during the thermal ablation operation.

This objective is achieved according to the present invention by a system and a method for automatic planning of a minimally invasive thermal ablation according to the object of the independent claims. Dependent claims present further advantages of the invention.

The present invention proposes, in particular, to use a neural ordinary differential equations (ODE) setup for automatically outputting a planning of a minimally invasive thermal ablation, wherein the planning includes in particular a number of needles and, for each needle, a trajectory, and additionally or optionally, for each needle, an ablation power and/or a duration during which ablation power has to be applied.

With the foregoing and other objects in view there is provided, in accordance with the invention, a computer-implemented method for automatic planning of a thermal ablation of a target object—hereafter "TO", e.g. a biological object like a tumor, located within (i.e. inside) a biological body (i.e. at a measurable depth inside the biological body, the depth being measured from an external surface, e.g. skin, of the biological body), e.g. a human or animal body, the method comprising:

acquiring or receiving one or several images of the target object within the biological body, the acquired images being notably configured for enabling a determination of a position (and optionally size and/or shape, notably from the position) of the TO, as well as a position of an external surface of the biological body. In other words, the information included within the acquired or received images enables the determination of a position of the TO, and the position of the external surface of the biological body. The external surface is the external surface of the biological body considered for the insertion of one or several RF ablation needles. For instance, the images are computed tomography (CT) images configured for showing the TO or a part of the latter, and/or its surrounding biological body, notably up to the external surface of the biological body, wherein the external surface is preferably the closest biological body external surface to the TO;

determining a position of the TO within the biological body from the received or acquired images of the biological body;

determining a position of the external surface of the biological body with respect to the position of the TO from the received or acquired images;

optionally, determining a position of one or several secondary biological body objects—hereafter "OAR", e.g. organs at risk during the thermal ablation, from the received or acquired images. By "position" of the TO or external surface or OAR, it has to be understood the set of points (or voxels) within an image, e.g. a 3D image, or the set of points (or voxels) in a coordinate system within which the TO, biological body and optionally OAR are represented, that belong to the TO, or respectively external surface or OAR. From this set of points, it is possible then to determine for instance the size, shape, center of the TO or external surface or OAR and their relative positions;

acquiring, for an initial set of N RF ablation needles usable for carrying out the thermal ablation, with N typically smaller or equal to 10, and for each type of RF ablation needles of the initial set, a set of characterizing features that are common to all RF ablation needles belonging to a same type, the set of characterizing features including at least one fixed parameter and/or at least one variable parameter, wherein the fixed parameter(s) is (are) for instance a geometrical characteristic (e.g. length, tip diameter, shape of the needle), and wherein the variable parameter(s) is(are) for instance an ablation shape and/or volume (e.g. min. ablation volume and/or maximum ablation volume, wherein the ablation volume is for instance a sphere centered on the needle tip, or an ellipsoid extending along a predefined needle length including its tip) in function of an ablation power and duration;

feeding into a neural ODE algorithm at least one of the characterizing feature (e.g. at least length and maximum ablation volume), the position of the external surface, the position of the TO, optionally the position of each OAR, the neural ODE algorithm being configured for outputting at least one thermal ablation plan, each plan including a final set of the RF ablation needles required for ablating the TO, the final set including $N\_F \leq N$ RF ablation needles, and for each RF ablation needle of the final set, its type, its trajectory from the external surface, and optionally, a value for the variable parameter(s);

providing the plan through an interface configured for guiding a clinician to realize the thermal ablation of the TO.

Preferentially, the obtained trajectories, outputted within each plan according to the invention, are used as a guide for a clinician. For instance, the trajectories might be automatically projected or overlaid on images, e.g. real time images, of the biological body, or insertion position of each needle might be directly projected on the external surface of the biological body, wherein the insertion position (or insertion point) of a needle might be defined as the intersection of the needle trajectory and the external surface. Preferentially, the sets of trajectories or the trajectories which are associated to the best scores are automatically selected and directly projected or overlaid on the images, or automatically proposed to the clinician who can select a set of n trajectories or a single trajectory for having the latter then automatically displayed or overlaid on the images.

With the objects of the invention in view, there is also provided a system configured for automatically planning a minimally invasive thermal ablation by carrying out the steps of the previously described method, the system comprises for instance:

optionally, an imaging system, like a CT imaging system, configured for acquiring images, e.g. 3D images, of the biological body and target object;

a memory or database for storing the acquired images and characterizing features of RF ablation needles usable for the thermal ablation;

a processing unit including a processor, the processing unit being configured for processing the acquired images;

optionally a display for displaying the acquired images; characterized in that the processing unit is configured for automatically carrying out the previously described method.

The foregoing has broadly outlined the features and technical advantages of the present disclosure so that those skilled in the art may better understand the detailed description that follows.

Additional features and advantages of the disclosure will be described hereinafter that form the object of the claims. Those skilled in the art will appreciate that they may readily use the concept and the specific embodiment disclosed as a basis for modifying or configuring other structures for carrying out the same purposes of the present disclosure.

Other features which are considered as characteristic for the invention are set forth in the appended claims.

Although the invention is illustrated and described herein as embodied in a method and a system for automatic planning of a minimally invasive thermal ablation and a method for training a neural network, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE FIGURES

FIG. 2 is a bock diagram of a system with images for automatically planning a minimally invasive thermal ablation according to the invention;

FIG. 3 is a flowchart of a method for automatic planning of a thermal ablation of a TO according to the invention.

DETAILED DESCRIPTION OF THE INVENTION

FIGS. 1 to 4, discussed below, and the various embodiments used to describe the principles of the present disclosure in this patent application are by way of illustration only and should not be construed in any way to limit the scope of the disclosure. Those skilled in the art will understand that the principles of the present disclosure may be implemented in any suitably disposed device. The numerous innovative teachings of the instant application will be described with reference to exemplary non-limiting embodiments.

Figure 1:
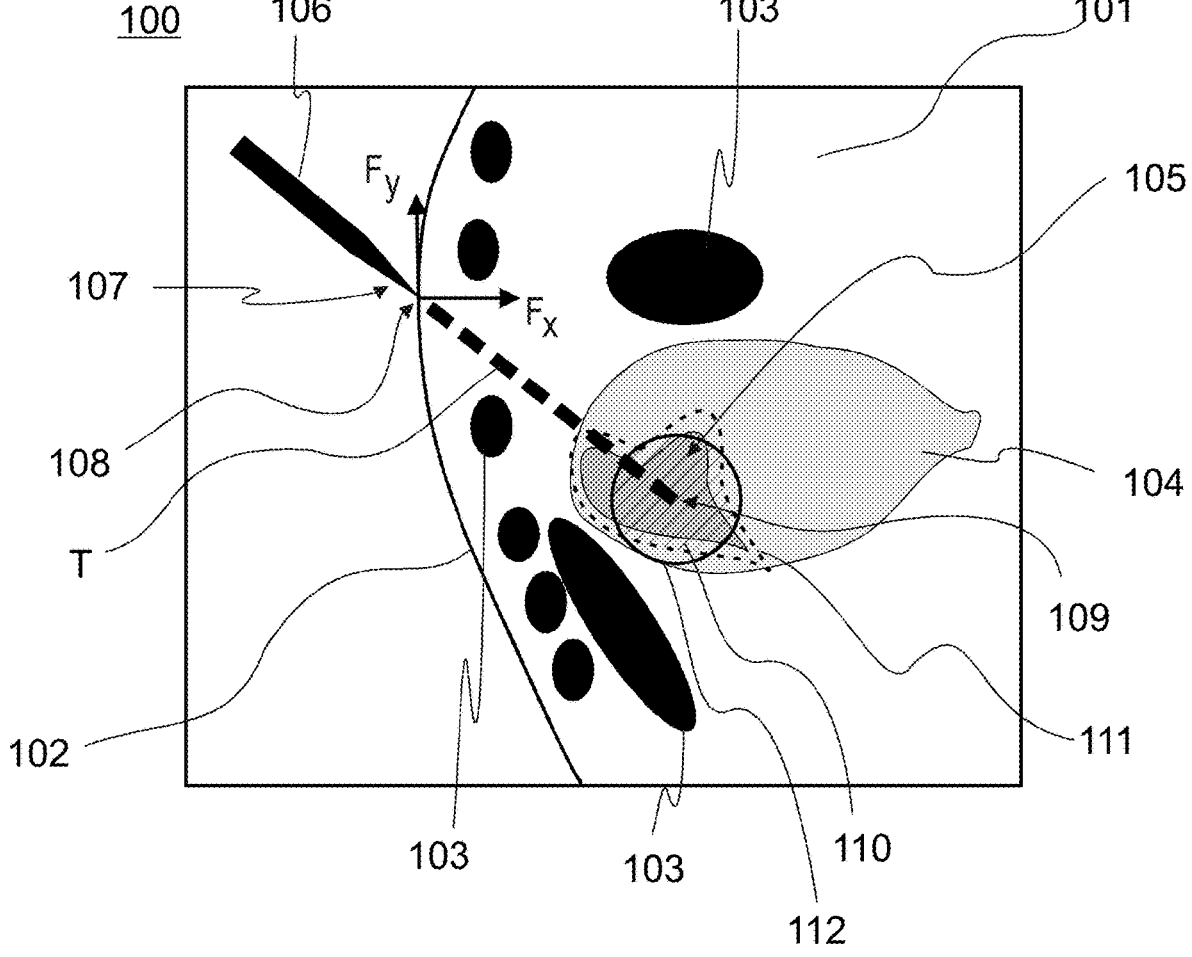
FIG. 1 is a diagrammatic view illustrating a thermal ablation technique involving a RF ablation needle.

Referring now to the figures of the drawings in detail and first, particularly, to FIG. 1 thereof, there is seen a diagrammatic illustration of the thermal ablation technique of a TO 105 located within a biological body 101, and involving one or several RF ablation needles 106 having a positioning on an external surface 102, e.g. skin, of the biological body 101, which is of crucial importance for determining the trajectory T from an insertion point 108 until a final position 109 located within the TO 105 that enables ablation of a maximal volume of the TO 105. For the purpose of the present illustration, the TO 105 is for instance a tumor located within a liver 104 of a patient. In particular, the trajectory T of each RF ablation needle (also simply called "needle") has to avoid any OAR 103. Therefore, each needle tip 107 has to be correctly positioned on the external surface 102 and according to well defined angles with respect to the external surface 102 in order to follow the trajectory T. Advantageously, the present invention enables a determination of the trajectory T for each needle of a set of needles, and thus its positioning with respect to the external surface 102, that enables optimal ablation of the TO 105. For each needle, and in function of its trajectory and own characteristics (e.g. ablation volume, length, etc.), an ablation coverage 110 might be automatically calculated by the neural ODE algorithm according to the invention so that it becomes possible to rapidly determine which final set of needles enables achievement of a total ablation coverage (that is typically the union of the ablation coverage of each needle composing a needle set) that is equal to or greater than a predefined ablation coverage 111. The latter might for instance, and as shown in FIG. 1, surround the whole TO 105. In particular, for each needle 106, an ablation zone 112 might be defined.

The ablation zone 112 is shown in FIG. 1 as a sphere centered on the needle tip 107 at the final position 109. The ablation coverage 110 of a needle 106 is the part of the sphere, i.e. of the ablation zone 112, that covers (or intersects or overlaps, i.e. that shares identical positions with) a zone or volume that has been defined as the predefined ablation coverage 111 (i.e. a zone or volume that should be ablated and which includes the TO 105 and optionally a margin or layer as explained below), the ablation coverage 110 corresponding to the hatched part in FIG. 1. The goal is to find the minimum number of needles and associated trajectories for which the union of their corresponding ablation coverages is equal to or greater than the predefined ablation zone 111 while being preferentially minimally invasive. The predefined ablation zone 111 includes typically the TO 105 and optionally the layer of predefined thickness or margin (measured notably radially from the external surface of the TO 105) that surrounds the TO 105 and which makes the predefined ablation coverage 111 bigger than the TO 105 and thus surrounding the latter. The predefined ablation coverage 111 is thus a zone or volume within the biological body 101 that shall be covered by the thermal ablation, i.e. that needs to be thermally ablated by using the needles 106 in order to increase the probability of having the whole TO 105 ablated and to prevent recurrence after ablation operations.

FIG. 2 schematically illustrates an embodiment of a system 200 according to the invention. The system 200 is configured for automatically planning a minimally invasive thermal ablation. The system 200 includes:

optionally, an imaging system 201, e.g. a CT imaging system, for acquiring images 206 of the biological body 101 that enable a determination of at least the position and optionally some characteristics (e.g. size, shape, etc.) of the TO 105;

a memory 203 for storing the acquired images 206. The memory might also be used for storing characterizing features of the RF ablation needles 106 that are usable for the thermal ablation;

a processing unit 202 including a processor, the processing unit being configured for processing the acquired images 106. The processing unit 202 is connected to the imaging system 201 and to the memory 203. The processing unit 202 preferentially includes the memory 203;

an interface 204, e.g. a display for displaying the acquired images 206.

The system 200 according to the invention is characterized in that its processing unit 202 is configured for carrying out the steps of the method according to the invention, which will be described in more details with reference to FIGS. 3 and 4, wherein FIG. 3 describes the different steps of the method 300 preferentially implemented by using the system according to FIG. 2, and FIG. 4 describes an example of an iteration process implemented by the neural ODE algorithm according to the invention.

At step 301, the processing unit 202 acquires one or several images 206 of the TO 105, for instance, from the imaging system 201 or from a database or memory. The acquired images 206 are images of the biological body 101 and preferentially includes the TO 105, or at least enables a determination of at least the position, optionally size and shape of the TO 105 within and with respect to the biological body 101.

At step 302, the processing unit 202 automatically determines the position, and optionally the size and shape, of the TO 105 within the biological body 101 from the acquired images. In other words, the acquired images 206 are used for automatically detecting and locating the TO 105 with respect to the biological body 101. For this purpose, and as known in the art, a common frame of reference might be used. Preferentially, segmentation techniques might be implemented by the processing unit 202 for determining the shape and/or size of the TO 105. Segmentation techniques, like image segmentation used in MRI, are well-known to the skilled person and do not need to be further described in the present document.

At step 303, the processing unit 202 is configured for automatically determining, from the acquired images, the position of the external surface 102 of the biological body 101 with respect to the position of the TO 105. Again, known in the art techniques might be used for this purpose.

At step 304, and optionally, the processing unit 202 is configured for determining, from the acquired images, a position of one or several OAR 103 within the biological body 101. By position of the OAR, or TO, it is notably referred to the set of positions within the biological body that are occupied by respectively the OAR, TO. This set of positions enables for instance a determination of the shape of the TO or respectively OAR. As already mentioned, techniques for detecting, locating, determining the size and shape of TOs or OAR are well known and not the subject of the present invention.

At step 305, the processing unit 202 acquires, for an initial set of N RF ablation needles 106, a set of characterizing features that are common to all RF ablation needles 106 belonging to the same type. Typically, FIG. 4 shows such an initial set 401 of RF ablation needles 106. The initial set 401 represents or includes the RF ablation needles 106 that are at the disposal of a clinician for carrying out the thermal ablation of the TO 106. It includes for instance two needles 106 of type A, noted hereafter $E^A$, one needle of type B, noted hereafter $E^B$, and one needle of type C, noted hereafter $E^C$. The needles $E^A$ are for instance shorter than the needle $E^B$, while the needle $E^C$ is characterized by a curved tip contrary to the types A and B of needles which are characterized by a straight tip. For each of the needle types A, B, and C, included within the initial set 401, a set of characterizing features including for instance the length of the needle, the tip diameter, tip curvature, needle diameter, etc., might be stored in a memory or database of the system 200.

At step 306, the processing unit 202 is configured for feeding into a neural ODE algorithm at least one of the characterizing feature, the position of the external surface 102, the position of the TO 105, optionally the position of the OAR(s) 103, wherein the neural ODE algorithm is configured for outputting at least one thermal ablation plan. The neural ODE algorithm might be encoded in a memory of the processing unit 202 or of the system 200. According to the present invention, each thermal ablation plan includes useful information for the clinician who is going to carry out the thermal ablation. In particular, each plan includes a final set 471 of the RF ablation needles 106 required for ablating the TO 105, the final set including N_F≤N RF ablation needles 106, and for each RF ablation needle 106 of the final set, its type, its trajectory T from the external surface 102, and optionally, a value for the variable parameter(s) and/or a score configured for indicating a degree of invasiveness for the final set, wherein the higher the score, the less invasive the thermal ablation.

At step 307, the processing unit 202 is configured for providing the plan through an interface 204, e.g. through a display, wherein the plan is configured for guiding the clinician to realize the thermal ablation of the TO 105 by showing or displaying, notably in real time, a current real position of a RF ablation needle used by the clinician with respect to the determined trajectory T for the needle. Typically, according to the present invention, the processing unit 202 will output one or several plans, each plan indicating the final set of needles to be used and for each needle its trajectory and type in order to achieve, when considering all needles of the final set, an ablation coverage that is at least equal to the predefined ablation coverage. Preferentially, the clinician can then select the most appropriate plan, e.g. by considering the score associated with each final set and choosing the highest score. The processing unit 202 might then automatically start a guidance process, wherein the trajectory determined for each needle of the final set is used as a guide for guiding the clinician, each trajectory being for instance used for showing/projecting, in real time, the insertion point of the concerned needle on the external surface of the biological body, and/or for comparing the current position of the needle with its position resulting from the calculated trajectory. For instance, the interface 204 according to the invention may include a projection system, controlled by the processing unit 202, and configured for projecting a trajectory T determined for a needle of a final set on a display or on the external surface of the biological body or as overlay on real time images of the biological body. In this way, a continuous guidance might be provided to the clinician, indicating for instance additionally the ablation power to be used for each needle, its duration, the depth of insertion, etc.

In particular, in order to determine the final set 471 of RF ablation needles 106, the neural ODE algorithm according to the invention is configured for automatically starting an iteration process. The latter is schematically illustrated in FIG. 4. It includes notably one or several creations of one or several needle sets from the initial set 401 of needles. FIG. 4 shows for instance a creation of three needle sets, namely a first needle set 411 including two needles of type A and one needle of type B, a second needle set 412 including one needle of each type A, B, C, and a third needle set 413 including two needles of type A and one needle of type C. In each needle set including n needles, $E^T_i$ is used for identifying the $i^{th}$ needle of the needle set and specifying its type T, wherein i=1, . . . , n. Further details about the creation of the needle sets will be provided hereafter.

The iteration process is further configured for incrementally populating the created needle sets by successively adding one needle to the needle sets either until obtaining at least one needle set including a number n=N_F of needles, with 1:5≤N_F≤N, that enables achieving a predefined ablation coverage 111 for the TO 105 (case I) or until reaching the maximum number n=N of needles that can be included in each created needle set (case II). In the latter case (case II), if none of the needle set(s) including N needles enables to achieve the predefined ablation coverage 111 for the TO 105, then the iteration process stops, and the neural ODE algorithm is configured for sending and/or displaying a message indicating that the predefined ablation coverage 111 cannot be achieved. According to case (I), the iteration process is thus configured for stopping when obtaining the needle set(s) including N_F needles, each of them becoming a so-called final set 471 of needles which is then included in a plan provided as output by the ODE algorithm.

The present invention thus proposes to increase a number n of needles to be used for the thermal ablation by incrementally populating one or several needle sets and determining whether, for such number n of needles, trajectories exist that will enable a minimally invasive thermal ablation of the TO 105. The iteration process starts notably with one or several needle sets including a single needle, i.e. n=1, and iteratively increments the number n of needles by adding one additional needle in the needle set(s) until either reaching a number n=N_F≤N of needles for which the predefined ablation coverage defined for the TO 105 is achieved or reached (i.e. the union of the different ablation coverages of the considered needles covers, i.e. integrally overlaps, the predefined ablation coverage), or the number n=N of needles is reached (e.g. without achieving the predefined ablation coverage). FIG. 4 illustrates the specific case wherein N=4 needles, and N_F=3 needles, which means that a final set 471 including 3 needles enabled to achieve an ablation coverage 110 that is at least equal to the predefined ablation coverage 111 (for instance, according to FIG. 1, it would correspond to an ablation coverage that covers the TO 105 plus a surrounding margin), while the trajectories defined for each of the needles of the final needle set ensure the minimally invasive thermal ablation.

In particular the iteration process includes a step (i) and a step (ii) which can be described as follows:

at step (i), for n=1, the neural ODE algorithm is configured for:

creating, from the initial set 401, and for one or several or each type of needle of the initial set 401, a needle set including n=1 RF ablation needle of the concerned type, and determining or acquiring or selecting, notably automatically, at least one, preferentially several, initial positions for the needle tip of the RF ablation needle of each created needle set. For instance, when referring to FIG. 4, the neural ODE algorithm will preferentially create the same number of needle sets as the number of different needle types, wherein the created needle sets are each populated with a needle of a different type. In the example of FIG. 4, 3 needle sets are therefore created from the initial set 401, namely a first needle set $(E^A_1)_{n=1}$ including only the needle $E^A_1$, a second needle set $(E^B_1)_{n=1}$ including only the needle $E^B_1$, and a third needle set $(E^C_1)_{n=1}$ including only the needle $E^C_1$. The neural ODE algorithm further associate to each of the created needle set $(E^T_1)_{n=1}$ one or several P-set $(P^p_1)$ defining each an initial position $P^p_1$ for the needle tip of the considered needle set, wherein $P^p_i$ is used for identifying the initial position defined for the $i^{th}$ needle of the considered needle set, wherein the initial position is defined within the $p^{th}$ P-set, wherein p=1, . . . , M, M being the number of created P-sets for the considered needle set. According to the present invention, each initial position included in a P-set might have been determined randomly by the neural ODE algorithm, or might have been calculated or determined, notably by the neural ODE algorithm, for maximizing the ablation coverage of the TO surrounded, optionally, by the margin or layer.

In other words, the neural ODE algorithm might be configured for creating as much needle sets as the number of the different types of needles, wherein each needle set includes n=1 needle of a specific type, and wherein for the needle of each set, the at least one, preferentially several, initial positions are assigned through the P-set(s) associated to each needle set. In particular, each initial position is preferentially located either within the volume of the TO or within a predefined area on the external surface, the predefined area depending for instance on the distance between the TO and the surface and needle characteristics, such as its length. Preferentially, all initial positions are located within the volume of the TO or within the predefined area. In particular, the initial positions are randomly determined;

selecting, for the needle of each needle set, at least one characterizing feature. The selected feature is preferentially the ablation volume and shape characterizing the needle;

for each initial position assigned to the needle tip of a needle of a needle set, and for each needle set, automatically using the initial position, the position of the TO, the characterizing feature(s) selected for the needle for which the initial position has been assigned, the position of the external surface, optionally the position of one or several OARs as inputs in a neural network $g_{n=1}$ whose weights have been optimized for minimizing a loss function $l_{n=1}$ related to a volume of non-ablated TO, and wherein $g_{n=1}$ is configured for outputting the force to be applied to the needle tip in function of the time t for minimizing the loss function. The force is preferentially noted $F^p_i(t)$ that is the force applied to the tip of the $i^{th}$ needle of the needle set when considering the $p^{th}$ P-set of initial position(s). Optionally, and additionally, the loss function might be related to a volume of ablated healthy tissue and/or a distance between a needle trajectory and the OAR(s) if the latter is (are) used as input(s);

from the previously obtained force(s), notably from and for each previously obtained force, automatically determining all needle trajectories T that enable to achieve an ablation coverage 110 defined for the TO 105 that is greater or equal to the predefined ablation coverage 111—according to the present invention, for each initial position $P^p_i$ considered for a needle $E^T_i$, a force $F^p_i$ is outputted by the neural network, and a trajectory $T^p_i$ is obtained, wherein $T^p_i$ is used for identifying the trajectory obtained for the $i^{th}$ needle of the considered needle set when using the $p^{th}$ P-set for defining the initial position of the needle tip, and then only trajectories that enable to achieve an ablation coverage greater or equal to the predefined ablation coverage are taken into consideration for determining the final set—, and if one or several of such trajectories exist, then stopping the iteration (wherein N_F=1) and providing as output, each needle set (the provided needle set becomes the so-called final set) for which such a trajectory has been determined, and for each needle set, at least the type of needle, and for the needle, all trajectories from the external surface until reaching a final position within the TO 105 that enabled to achieve the ablation coverage 110 greater or equal to the predefined ablation coverage 111, and optionally, for each of the trajectories, a score that is a function of a loss value obtained for the loss function for the considered trajectory and/or of a ratio of the achieved ablation coverage to the predefined ablation coverage, otherwise, if no trajectory enables to achieve an ablation coverage of the TO that is greater or equal to the predefined ablation coverage, then increasing the number of needles to be used by adding one additional needle of the initial set 401 to each needle set, and starting step (ii). In particular, for each needle set, a needle of a different type or of the same type as the needle being already part of the set might be added;

and wherein, at step (ii), for a number n of needles, with 1<n≤N, the neural ODE algorithm is configured for:

optionally, creating one or several additional sets of n needles, so that the needle set(s) created at step (i) together with the additional needle set(s) created at step (ii) represent each a different combination of the needle types, and preferentially all combinations of the needle types and/or automatically removing any duplicate of a needle set, wherein a removed needle set is not further processed. A needle set is a duplicate of another needle set if they include the same number of needles and they share the same number of needles for each type that they include. In the following, the wording "needle set" will refer equally to a needle set created at step (i) or at step (ii). Therefore, according to the present invention and preferentially, different needle sets of n needles combining one or several types of needles are considered. Combination rules might be used for creating the different sets of n needles, so that for instance all possible combinations of the different types of needles be obtained and used for populating the needle sets. In particular, in FIG. 4, the created first, second, and third needle sets are shown according to their status at the $3^{rd}$ iteration (n=3), i.e. the number of needles within the first needle set $(E^A_1)_{n=1}$ has been successively increased by adding the needle $E^A_2$ to obtain the needle set $(E^A_1,E^A_2)_{n=2}$, and then by further (at the next iteration) adding the needle $E^B_3$ to obtain the so called first needle set 411 $(E^A_1,E^A_2,E^B_3)_{n=3}$. The same applies mutatis mutandis to the needle sets $(E^B_1)_{n=1}$ and $(E^C_1)_{n=1}$ for resulting in the second needle set $(E^B_1,E^A_2,E^C_3)_{n=3}$ 412 and third needle set $(E^C_1,E^A_2,E^A_3)_{n=3}$ 413. As it can be seen from the example provided in FIG. 4, at the $4^{th}$ iteration, populating the first, second and third needle sets will result in the following needle sets $(E^A_1,E^A_2,E^B_3,E^C_4)_{n=4}$, $(E^B_1,E^A_2,E^C_3,E^A_4)_{n=4}$ and $(E^C_1,E^A_2,E^A_3,E^B_4)_{n=4}$, which are duplicates, the neural ODE algorithm keeping then only one of the needle sets, e.g. the first needle set $(E^A_1,E^A_2,E^B_3,E^C_4)_{n=4}$, the other being not further processed. In particular, once the needle sets for n=1 created, the neural ODE algorithm may iteratively populate the latter by randomly adding to the needle set one of the needles of the initial needle set that was not yet added to the concerned needle set, and afterwards it can check for duplicate in order to avoid any redundancy. Of course, other methods for creating and then populating the needle sets might be used;

determining or acquiring or selecting, notably automatically, at least one, preferentially several, sets of n initial positions, i.e. one or several "P-sets", for each of the created needle sets including n RF ablation needles, wherein each of the n initial positions of a P-set determined or acquired or selected for a needle set defines an initial position for the tip of one of the n needles of the needle set. Each needle of a needle set including n needles is thus assigned an initial tip position in each of the P-sets of n initial positions. Otherwise the, each P-set of n initial positions provides an initial position for the tip of each of the n needles of the considered needle set, wherein two different P-sets of a same needle set differ in that the initial position for the tip of at least one of the n needles is different. In particular, the tip of each needle of a same needle set is assigned a different initial tip position. According to the present invention, each initial position is preferentially located either within the volume of the TO or within a predefined area on the external surface, the predefined area depending for instance from the distance of the target from the surface and needle characteristics, such as its length. As previously explained, preferentially, all initial positions are located within the volume of the TO or within the predefined area. In particular, the initial positions are randomly determined.

Figure 4:
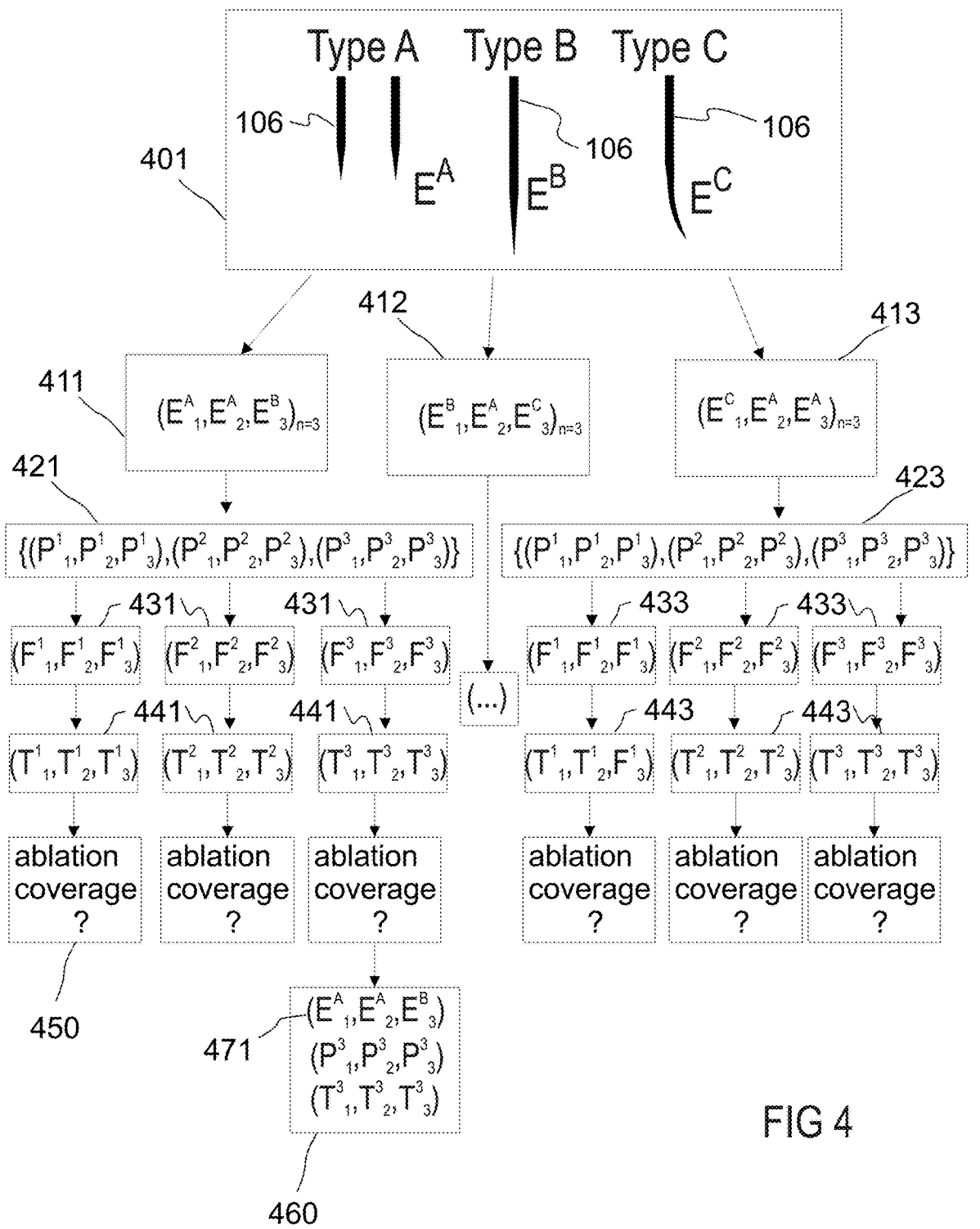
FIG. 4 is a flowchart of an iteration process implemented by the Neural ODE algorithm according to the invention.

FIG. 4 shows, in box 421 and 423, examples of P-sets created respectively for the first needle set 411 and the third needle set 413. For each of the first and second needle set, 3 P-sets have been created, namely a first P-set $(P^1_1,P^1_2,P^1_3)$, a second P-set $(P^2_1,P^2_2,P^2_3)$, and a third P-set $(P^3_1,P^3_2,P^4_3)$. Each P-set associates to each needle of the considered needle set an initial position. Each P-set for a same needle set is different, but a same set of P-sets might be used for the different needle sets as shown in FIG. 4, wherein the box 421 and 423 include the same set of P-sets;

selecting, for each needle of each needle set, at least one characterizing feature;

for each P-set of n initial positions assigned to the needle tips of the n needles of a needle set, and for each needle set, automatically using the n initial positions defined by the considered P-set, the position of the TO 105, the selected characterizing feature(s) of each of the n needles of the needle set, the position of the external surface 102, optionally the positions of one or several OARs 103 as inputs in a neural network $g_n$ whose weights have been optimized for minimizing a loss function $l_n$ related to a volume of non-ablated TO, and which is configured for outputting the respective force $F^P_i(t)$ to be applied to each of the n needle tips in function of the time t for minimizing the loss function. When considering a needle set of n needles $E^T_1, \ldots, E^T_n$, the set of forces $F^P_1(t), \ldots, F^P_n(t)$ represents the respective forces $F^P_i$ applied to the tip of the needle $E^T_i$, with i=1, . . . , n. Optionally, and additionally, the loss function might be related to a volume of ablated healthy tissue and/or a distance between a needle trajectory and the OAR(s) if the latter is (are) used as input(s).

For instance, for each P-set $(P^P_1, P^P_2,P^P_3)$, with p=1, . . . , 3, shown in box 421 and 423, a set of forces $(F^P_1, F^P_2,F^P_3)$ 431, 433 is obtained as output from $g_{n=3}$ when using as input the P-set $(P^P_1, P^P_2,P^P_3)$, the position of the TO 105, the length and ablation volume of each of the n needles of the considered needle sets 411 or 413, and the position of the external surface 102;

from the forces previously obtained, notably all previously obtained forces, automatically determining, for each needle set, all sets of n trajectories T that enable to achieve an ablation coverage 110 of the TO 105 that is greater or equal to the predefined ablation coverage 111, wherein a different set of n trajectories is determined for and from each P-set defined for the considered needle set, wherein each needle of the needle set is assigned to a single one of the n trajectories. In other words, for each needle set, one or several sets of n trajectories is determined from the obtained forces to be applied to the needle tip of the needles of the considered needle set, wherein each set of n trajectories is thus associated to the P-set of n initial positions that was used as input to $g_n$ for calculating the forces, wherein each needle of the needle set is thus assigned an own trajectory, and wherein only sets of n trajectories which enable to achieve an ablation coverage 110 at least equal to the predefined ablation coverage 111 are taken into consideration for creating the final set.

According to the example presented in FIG. 4, for each P-set provided in the boxes 421, 423, a set of forces is $(F^P_1, F^P_2,F^P_3)$ 431, 433 is obtained, and for each of the sets of forces 431, 433, a set of trajectories $(T^P_1, T^P_2,T^P_3)$ 441, 443 is obtained. For each of the sets of trajectories, the neural ODE automatically determines 450, for each set of trajectories 441, 443, whether the ablation coverage that can be obtained through the considered trajectories defined in the considered set of trajectories is equal or greater that the predefined ablation coverage.

According to the present invention, if one or several sets of such sets of n trajectories that enable to achieve an ablation coverage at least equal to the predefined ablation coverage exist, then the processing unit 202 is configured for stopping the iteration (wherein N_F=n) and providing as output, each needle set for which such a set of n trajectories has been determined, and for each of the needle sets provided as output, at least the needle type of each of the n needles included in the concerned needle set, and all sets of n trajectories that have been determined for the needle set as enabling to achieve an ablation coverage of the TO that is greater or equal to the predefined ablation coverage, wherein for each set of n trajectories, the trajectory of the needle tip of each needle of the needle set is determined by the processing unit 202 from the external surface until reaching a final position within the TO, and optionally, further outputting a score for each considered set of n trajectories, wherein the score is a function of a loss value obtained for the loss function for the considered set of n trajectories and/or of a ratio of the achieved ablation coverage to the predefined ablation coverage, otherwise, if no set of n trajectories enables to achieve an ablation coverage of the TO that is greater or equal to the predefined ablation coverage, then increasing the number n of needles to be used by adding one additional needle to the needle set and repeating step (ii) unless step (ii) has already been run for n=N, in which case, the neural ODE algorithm is configured for automatically sending a message indicating that the predefined ablation coverage cannot be achieved.

For instance, as illustrated in FIG. 4, only the set of trajectories ($T^3_1$, $T^3_2$, $T^3_3$) has been found by the neural ODE algorithm as enabling to achieve an ablation coverage at least equal to the predefined ablation coverage. In order to get this result, the neural ODE algorithm might determine for each needle of the needle set and along the trajectory $T^3_i$ of each of the needles, the TO part or TO volume that is included within the ablation volume, e.g. max. ablation volume, of the considered needle when moving along the trajectory, calculating for instance the union of the TO parts or volumes obtained for each needle in order to determine whether the union is greater or equal to the predefined ablation coverage. If this is the case, it names the considered needle set as a final set and outputs the latter together with the associated P-set and set of trajectories, as shown in box 460.

Thanks to the previously described iteration, the neural ODE algorithm is able to determine one or several final sets of RF ablation needles which, according to the determined trajectories for each of the needles of the final set, is able to achieve the predefined ablation coverage. For this purpose and preferentially, it needs to use a set of n neural networks, $g_1, \ldots, g_N$, wherein each neural network $g_n$ has been trained to determine the force to apply on each needle tip of a set of n needles (i.e. for each needle tip of a set of n needles, a force $F^p_i$ is determined through the neural network $g_n$).

In particular, for a needle set including n=1 needle, the ablation coverage is defined as the volume of the TO or of the zone including the TO and the surrounding layer/margin (i.e. of the predefined ablation coverage) that is included within the ablation volume of the considered needle when considering each position of the needle trajectory from its insertion position until reaching its final position at which the needle will be activated (i.e. each of the positions at which the needle will perform thermal ablation according to the considered ablation volume). Of course, the ablation volume might be a function of the power applied to the needle and/or duration of application of the power. In particular, for a needle set including n>1 needles, the ablation coverage is defined as the union of the n TO volumes (or of the n predefined ablation coverage parts or volumes) that are each included within an ablation volume of one of the n needles of the considered set of needles when considering each position of the associated needle trajectory from its insertion position until reaching its final position at which the considered needle is active, i.e. is performing thermal ablation. Indeed, each needle can be active only at its final position, or at several positions along its trajectory. For each position at which a needle is active, an ablation volume can be considered and the intersection between the considered ablation volume and predefined ablation coverage provides information regarding the remaining parts of the predefined ablation coverage that still should be ablated by other needles. The predefined ablation coverage is typically the volume of the TO, or a volume surrounding the whole target object according to a predefined gap (i.e. according to the layer or margin) measured from the external surface of the TO.

According to the present invention, the weights of each neural network $g_n$ have been optimized by solving an optimization problem that seeks to minimize the loss function $l_n$ with respect to a parameter w representing the weights of the neural network $g_n$, wherein the optimal parameter $w_n^*$ minimizing the loss function $l_n$ is obtained by solving $$w_n^* = \arg\min_w l_n(u) \text{ in such a way that} \quad (Eq.\ 1)$$

$$\frac{d}{dt}u = f(u, g_n(u, w)) \text{ with } u(t=0) = u_0$$

wherein
$l_n$ is the loss function, which is related to the volume of non-ablated TO, the latter being for instance a function of the characterizing feature of each needle of a considered set of n needles, e.g. a needle ablation volume. Optionally, and additionally, as already mentioned, the loss function might be related to a volume of ablated healthy tissue and/or a distance between each needle trajectory and the OAR(s);
u is the state vector of the system, wherein the system includes the needle tip position and velocity of each needle of the considered set of n needles, the TO position, the external surface position, optionally the position of each OAR;
t is the time;
f is the time derivative of the system state describing the temporal evolution of the system;
$g_n$ is the neural network of parameter w and configured for receiving as input the state vector u;
w is the parameter representing the weights of the neural network $g_n$;
wherein $u_0$ represents the state of the system at time t=0, i.e. the initial position of the needle tip of each needle of the set of n needles;
In particular, the above-mentioned positions are defined with respect to a coordinate system or frame of reference, e.g. a 3D cartesian coordinate system.
According to the present invention, the dynamic motion of each considered needle $E^T_i$, i∈{1, . . . , n}, for a set of needles including n needles $E^T_1, \ldots, E^T_n$, is defined according to a system of ODEs wherein the needle tip acceleration $\ddot{r}_i$ is a function of the initial position of the needle tip, its velocity $\dot{r}_i$, and the force $F^p i$ applied to the needle tip in the three directions of the coordinate system, i.e. $F^p_{i,x}$, $F^p_{i,y}$, $F^p_{i,z}$, resulting in $$\ddot{r}_i = f\left(F_i^p, \dot{r}_i, x_{i,0}^p, y_{i,0}^p, z_{i,0}^p\right),$$

$$\text{i.e.} \begin{cases} \ddot{x}_i = f_x\left(F_{i,x}^p, \dot{x}_i, x_{i,0}^p, y_{i,0}^p, z_{i,0}^p\right) \\ \ddot{y}_i = f_y\left(F_{i,y}^p, \dot{y}_i, x_{i,0}^p, y_{i,0}^p, z_{i,0}^p\right) \\ \ddot{z}_i = f_z\left(F_{i,z}^p, \dot{z}_i, x_{i,0}^p, y_{i,0}^p, z_{i,0}^p\right) \end{cases}$$

wherein the force F required to achieve an optimal trajectory for the tip of each needle of the set of n needles can be represented by a matrix, and is learned through the neural network $g_n$ according to:

$$F = g_n(u, w),$$

$$\text{i.e.} \begin{pmatrix} F_{1,x}^p, F_{1,y}^p, F_{1,z}^p \\ \dots \\ F_{n,x}^p, F_{n,y}^p, F_{n,z}^p \end{pmatrix} =$$

$$g_n\left(x_{1,0}^p, y_{1,0}^p, z_{1,0}^p, \dots, x_{n,0}^p, y_{n,0}^p, z_{n,0}^p, TO_{position}, OAR_{position}, w\right)$$

wherein $TO_{position}$ is the position of the TO and $OAR_{position}$ is an optional parameter which represents the position of the OAR, $P_i^p$ $(x_{i,0}^p, y_{i,0}^p, z_{i,0}^p)$ being the initial position of the needle $E^T_i$ of the considered needle set when considering the $p^{th}$ set of initial positions. Of course, if different OARs are considered, then $g_n$ is a function of the position of each considered OAR.

According to the present invention, each neural network $g_n$ is thus trained to learn the force F i.e. the matrix of the forces $F^p_i$ to apply on the needle tip of each needle $E^T_i$ of a set of n needles in order to achieve, for each needle of the set of n needles, an optimal trajectory that enables to minimize the loss function. Each needle trajectory is constrained by the dynamics defined by the function $f=(f_x, f_y, f_z)$. The neural network architecture for $g_n$ is preferentially a perceptron with an input layer, one hidden layer, and an output layer. Of course, other neural network architectures can be considered.

The present invention also proposes a method for training each neural network $g_n$. The method uses machine learning reinforced by ODEs modeling to determine the dynamic motion of the needle(s). It aims minimizing the loss function $l_n$, wherein the loss depends on the neural network weights. The method includes, for each neural network $g_n$, n=1, . . . , N:

receiving input training data, the input training data including sets of target object positions, optionally sets of OAR positions, sets including each n initial needle positions, wherein the initial positions are for instance randomly determined. Preferentially, synthetic data are automatically generated for increasing the input training data. For instance, from a real CT image of a biological body with one or several real target objects, e.g. tumors within a liver, to be ablated, the present invention proposes to create synthetic target objects by increasing and/or decreasing the size of one or several real target objects and changing the position of the real target object within the biological body (e.g. at different locations within the liver). Advantageously, the generation of synthetic data makes it possible to rapidly create input training data, generating for instance 10'000 synthetic images from the 170 CT images of a biological body;

using the input training data for training the neural network $g_n$ by solving Eq. 1, wherein the input training data are used as input to the Eq. 1 in order to determine the optimal parameter $w_n^*$ representing the weights of $g_n$ that enable to minimize the loss function $l_n$;

outputting the optimal parameter $w^*$. Considering then a set including n needles, the optimized trajectory for each needle of the set is obtained by solving $F=g_n(u, w_n^*)$, $w_n^*$ representing the optimized weights of the neural network $g_n$.

For a better understanding of the present invention, the following simplistic examples are provided, wherein a cartesian coordinate system is used for describing the system state:

Considering a simplified 2D set-up, wherein the external surface of the biological body is a skin considered as a straight line (y=0) on top of a liver and no organs at risks are considered (no OARs). In a first case, a needle starting point on the skin is considered as fixed, but the location of a TO, a tumor, varies within the liver. According to this simplistic set-up, the neural network needs to learn the optimal trajectory to reach the tumor and the loss function might be defined as:

$$l_1(u) = (x_{t=end} - x_{tumor})^2 + (y_{t=end} - y_{tumor})^2$$

wherein $(x_{t=end}, y_{t=end})$ is the final position of the needle tip in the biological body and $(x_{tumor}, y_{tumor})$ is the position of the tumor centroid. In this very simplistic illustration, the system dynamics to model the needle insertion into biological tissue can be written as follows, wherein for each direction, the needle velocity is egal to the force applied on the needle in this direction plus a term to model the resistance $R_p$ of the parenchyma:

$$\begin{cases} \dot{x} = F_x - R_p \cdot \dot{x} \\ \dot{y} = F_y - R_p \cdot \dot{y} \end{cases}$$

In such a case, a training can be performed by modifying the tumor location, for instance by keeping the tumor location on a straight line at x=−5, and varying its y coordinate between −5 and 5.

Considering again the simplified 2D set-up, wherein the external surface of the biological body is a skin considered as a straight line (y=0) on top of a liver, but this time, in a second case, an organ at risk is present. According to the second case, the tumor location is fixed within the liver at (x=0, y=−5), and the position $(x_{org}, y_{org})$ of the organ at risk varies. In this case, the needle starting point is fixed in the tumor. This time, the neural network needs to learn the shortest trajectory to reach the skin while avoiding the organ at risk. For this purpose, the loss function can be written as $$l_1(u) = 100 \cdot (y_{t=end} - y_{skin})^2 + 0.001 \cdot \max(F_x^2) + 0.001 \cdot \max (F_y^2)$$

In this case, trajectories that require more force to reach the skin are penalized, since they are not the shortest ones. The system dynamics to model the needle insertion into biological tissue can be written as follows, wherein in each direction, the needle velocity is egal to the force applied on the needle in the considered direction, plus a term to model the resistance $R_p$ of the parenchyma, plus an additional term to simulate a strong resistance $R_{org}$ to an insertion of the needle in the organ at risk modeled using a Heaviside function whose non-zero values only appear in the organs at risk:

$$\begin{cases} \dot{x} & = F_x - R_p \cdot \dot{x} - R_{org} \cdot \text{Heaviside}(x, y) \\ \dot{y} & = F_y - R_p \cdot \dot{y} - R_{org} \cdot \text{Heaviside}(x, y) \end{cases}$$

The training can then be made by modifying the position of the organ at risk within the biological body. The trained neural network can then be used for automatic planning of thermal ablations for similar systems.

Of course, the above-mentioned two examples are very simplistic and non-limiting illustrations of the present invention simply aiming a better understanding of the present concept. For real cases, i.e. more complex cases, the loss function and the system dynamics are adapted for taking into account the characteristics of the considered system.

At the end, the present invention makes it possible to provide automatic and fast patient-specific optimal ablation strategies, in particular, only from intra-operative CT images and within only few minutes in order to be compatible with clinical settings and decrease the procedural risks linked to prolongated interventional time. As explained earlier, the ODE algorithm is configured for taking as input such intra-operative CT images and is configured for providing, as output, one or several optimal thermal ablation plans, wherein each plan is going to define the number of needles, the corresponding ablation power and duration required to ablate completely the TO 105 with a minimal margin, e.g. 5 mm, around it, and the trajectories of the needles in the biological body avoiding the OARs, e.g. critical organs, structures like ribs, main hepatic blood vessels, etc. For instance, after the acquisition of a patient CT images, organs at risk, ribs, important blood vessels and tumors are automatically segmented by the system according to the invention. From this information, the power of AI embedded in the ODE algorithm is able to automatically and quickly estimate the optimal ablation strategies for the patient. Usually, the ODE algorithm will find quickly several thermal ablation plans, since, in most of the cases, there is not only a single solution. A clinician can then choose the preferable thermal ablation plan. During implementation of the chosen plan, the system according to the invention may provide guidance to the clinician by showing or displaying in real time a needle trajectory or a part of a needle trajectory as determined and defined in the thermal ablation plan versus the current, real, trajectory of the needle. Thanks to the present invention, thermal ablation planning becomes repeatable, operator-independent, less complex and less time consuming. For instance, it strongly simplifies thermal ablation of complex tumors which is today only possible in few of the best hospitals in the world where well experienced clinicians can perform such difficult procedures.

The main advantages of the present invention are the following:

an improved accuracy and simplicity of ablation planning: this invention enables the planning of ablation therapies, straightforward and complex. It allows a simpler operation less depending on the experience of the physician and also makes the ablation more precise and reproductible, leading to an increased success rate. As it highly decreases the complexity of the planning step, it will increase the number of patients who are candidates for curative treatment. Patients that are today treated with heavy liver surgery procedures could be thus treated with minimally invasive thermal ablation;

an improved ablation procedure duration: the present invention also drastically decreases the time spent for planning a thermal ablation, especially in the case requiring several needles. The planning is preferentially performed after a pre-operative CT just before the intervention with a patient under general anaesthesia (to have the patient in the same condition as he/she will be during the intervention). Moreover, the automatic and fast planning feature of the present invention is preferentially part of an end-to-end system for needle-based procedure, which makes the execution of the planned ablation simpler, and thus performed faster. Therefore, this invention enables cheaper and safer thermal ablations.

an improved ablation procedure outcome: the invention described in the present document also allows an analysis of the planned thermal ablation directly before an intervention. The ablation area/volume defined for each needle set can be compared to a TO area/volume plus an adequate ablation margin (i.e. to the predefined ablation coverage) to ensure a complete coverage of the TO. The automatic thermal ablation planning based on the ODE algorithm ensures that the resulted ablation does cover the TO with an adequate margin around it. This will further reduce the number of recurrences and therefore the number of second ablations needed to correct the results of non-complete ablations.

a faster and easier algorithm training: the advantages of using Neural ODEs instead of Deep Reinforcement learning is a faster and easier training phase of the algorithm resulting from using the underlying physics describing the insertion of a needle into biological tissue. It allows to narrow the exploration phase during the training of the algorithm to only situations that are physically relevant. By doing so and taking advantages of differentiable programming, the training phase can be simplified and faster.

To summarize, the present invention proposes a method and a system that enable to automatically provide a guiding to a clinician during a thermal ablation operation by providing to the latter different planning which enable to minimize the invasiveness of the thermal ablation.

LIST OF CITATIONS

[1] Laimer, G., Schullian, P., Jaschke, N., Putzer, D., Eberle, G., Alzaga, A., Odisio, B., Bale, R. (2019). Minimal ablative margin (MAM) assessment with image fusion: an independent predictor for local tumor progression in hepatocellular carcinoma after stereotactic radiofrequency ablation. European journal of radiology.

[2] Bale, R., Schullian, P., Eberle, G., Putzer, D., Zoller, H., Schneeberger, S., . . . & Oberhuber, G. (2019). Stereotactic radiofrequency ablation of hepatocellular carcinoma: a histopathological study in explanted livers. Hepatology, 70(3), 840-850.

[3] Bale R, Widmann G, Schullian P, et al. Percutaneous stereotactic radiofrequency ablation of colorectal liver metastases. Eur Radiol. 2012; 22(4):930-937.

[4] Schullian P, Manzi C, Oberhuber G, et al. Stereotactic radiofrequency ablation of hepatocellular carcinoma—A histopathological study in explanted livers. Hepatology

[5] Zhang, R., Wu, S., Wu, W., Gao, H., & Zhou, Z. (2019). Computer-assisted needle trajectory planning and mathematical modeling for liver tumor thermal ablation: A review. Mathematical Biosciences and Engineering, 16(5), 4846-4872.

[6] Bale, R., Widmann, G., & Stoffner, D. R. (2010). Stereotaxy: breaking the limits of current radiofrequency ablation techniques. European journal of radiology, 75(1), 32-36

The invention claimed is:

1. A computer-implemented method for automatic planning of a thermal ablation of a target object located within a biological body, the method comprising:

acquiring one or several images of the target object within the biological body;

determining a position of the target object within the biological body from the one or several acquired images;

determining a position of an external surface of the biological body with respect to the position of the target object from the one or several acquired images;

providing an initial set of N RF (radiofrequency) ablation needles including RF ablation needles of one or several types being usable for carrying out the thermal ablation, where N is a number of RF ablation needles of the initial set;

acquiring a set of characterizing features for each type of the one or several types of RF ablation needles in the initial set of N RF ablation needles, the set of characterizing features being common to all RF ablation needles of a same type, and the set of characterizing features including at least one of at least one fixed parameter or at least one variable parameter;

feeding into a neural ordinary differential equation algorithm the position of the external surface, the position of the target object, and at least one of the characterizing features;

configuring the neural ordinary differential equation algorithm for outputting at least one thermal ablation plan, each of the at least one thermal ablation plan including a final set of the RF ablation needles required for ablating the target object, the final set including N_F≤N RF ablation needles, and for each RF ablation needle of the final set, its type, its trajectory from the external surface, and optionally, a value for the at least one variable parameter, where N_F is a number of the RF ablation needles in the final set; and providing the at least one thermal ablation plan through an interface configured for guiding a clinician to realize the thermal ablation of the target object.

2. The computer-implemented method according to claim 1, which further comprises determining, from the acquired images, a position of one or several secondary biological body objects, the feeding including feeding the position of each secondary biological body object into the neural ordinary differential equation algorithm.

3. The computer-implemented method according to claim 1, which further comprises, configuring the neural ordinary differential equation algorithm for automatically starting an iteration process, the iteration process including one or several creations of one or several needle sets from the initial set of needles, and the iteration process being configured for incrementally populating the created one or several needle sets by successively adding one needle to the one or several needle sets either until obtaining at least one needle set including a number of needles enabling achievement of a predefined ablation coverage of the target object with the at least one needle set being the final needle set including N_F needles, or until reaching the number N of needles being a maximum number of needles that can able to be included in each created needle set.

4. The computer-implemented method according to claim 3, which further comprises including a first phase and a second phase in the iteration process, wherein in the iteration process n represents, for a current iterative phase, a current number of RF needles included in a considered created needle set, the value of n being iteratively changed at each iterative phase by addition of one needle;

wherein for the first step phase, n=1 and the neural ordinary differential equation algorithm is configured for:

creating, for at least one of the one or several types of needles of the initial set, a needle set including n=1 RF ablation needle of a concerned type, and determining or acquiring or selecting at least one initial position for a needle tip of the RF ablation needle of each created needle set;

selecting, for the needle of each needle set, at least one characterizing feature of the set of characterizing features;

for each initial position assigned to the needle tip of the needle of the needle set, and for each needle set, automatically using the initial position, the position of the target object, the needle characterizing feature for the needle for which the initial position has been assigned, the position of the external surface as inputs in a neural network $g_{n=1}$ with weights having been optimized for minimizing a loss function $l_{n=1}$ related to a volume of non-ablated target object, and wherein $g_{n=1}$ is configured for outputting the force F(t) to be applied to the needle tip as a function of the time t for minimizing the loss function;

from at least one force F(t) previously obtained, automatically determining all needle trajectories enabling achievement of an ablation coverage of the target object being greater than or equal to the predefined ablation coverage, and upon one or several of such trajectories existing, then stopping the iteration and providing as an output:

each needle set for which such a trajectory has been determined, each of the needle sets provided as an output becoming a final set with N_F=1;

and for each needle set provided as an output, provide at least the type of RF ablation needle and all trajectories from the external surface until reaching a final position within the target object enabled to achieve the ablation coverage greater than or equal to the predefined ablation coverage;

otherwise, upon no trajectory being enabled to achieve the ablation coverage of the target object being greater than or equal to the predefined ablation coverage, then increasing the number of needles to be used by adding one additional needle to each of the needle set, and starting the second phase;

at the second phase, with n varying from 2 to N_F and may reach the maximum N, the neural ordinary differential equation algorithm being configured for:

determining or acquiring or selecting at least one set of n initial positions for each of the created needle sets including n RF ablation needles, the set of n initial positions being P-set, wherein each of the n initial positions of a P-set defines an initial position for the tip of one of the n needles of the needle set associated with the P-set, each needle tip being assigned a different initial position, and two different P-sets for a same needle set differing in that the initial position defined for at least one of the needles of the needle set is different;

selecting, for each needle of the needle set, at least one characterizing feature;

for each P-set of each of the needle set, automatically using the n initial positions of the considered P-set, the position of the target object, the characterizing feature of each of the n needles of the needle set, and the position of the external surface as inputs in a neural network $g_n$ with weights having been optimized for minimizing a loss function $l_n$ related to a volume of non-ablated target object, and being configured for outputting the force to be applied to each of the n needle tips of the needle set as a function of the time t for minimizing the loss function;

from the forces previously obtained, automatically determining, for each of the needle set, all sets of n needle trajectories enabling achievement of the ablation coverage of the target object being greater than or equal to the predefined ablation coverage, a different set of n trajectories being determined for and from each P-set defined for the needle set, each needle of the needle set being assigned to one of the n trajectories, and upon one or several sets of such sets of n trajectories existing, then stopping the iteration and providing as an output:

each of the needle set for which such a set of n trajectories has been determined, each of the needle sets provided as an output becoming a final set with N_F=n;

and, for each of the needle set provided as an output, provide at least the needle type of each of the n needles included in the needle set, and all sets of n trajectories having been determined as enabling to achieve the ablation coverage of the target object being greater than or equal to the predefined ablation coverage, for each set of n trajectories, the trajectory of the needle tip of each needle of the needle set being determined from the external surface until reaching a final position within the target object, otherwise, upon no set of n trajectories enabling achievement of the ablation coverage of the target object being greater than or equal to the predefined ablation coverage, then increasing the number n of needles to be used by adding one additional needle to the needle set and repeating the second phase unless the second phase has already been run for n=N, in which case, the neural ordinary differential equation algorithm being configured for automatically sending a message indicating that the predefined ablation coverage cannot be achieved.

5. The computer-implemented method according to claim 4, which further comprises randomly determining at least one initial position.

6. The computer-implemented method according to claim 4, which further comprises carrying out the second step by first creating one or several additional sets of n RF ablation needles, so that the at least one needle set created at the first step together with the additional at least one needle set created at the second step each represent a different combination of the needle types.

7. The computer-implemented method according to claim 4, which further comprises locating each initial position either within the target object or on a predefined area of the external surface.

8. The computer-implemented method according to claim 4, which further comprises optimizing the weights of each neural network $g_n$ by solving an optimization problem configured for minimizing the loss function $l_n$ with respect to a parameter w representing the weights of the neural network $g_n$, wherein the optimal parameter $w_n^*$ minimizing the loss function $l_n$ is obtained by solving:

$$w_n^* = \arg\min_w l_n(u) \text{ in such a way that}$$

$$\frac{d}{dt}u = f(u, g_n(u, w)) \text{ with } u(t = 0) = u_0$$

wherein:

$l_n$ is the loss function, related to the volume of non-ablated target object;

u is a state vector of a system, the system including the needle tip position and velocity of each needle of the considered set of n needles, the target object position, the external surface position, and optionally the position of each secondary biological body objects;

t is a time;

f is a time derivative of a system state describing a temporal evolution of the system;

$g_n$ is the neural network of parameter w and configured for receiving as an input the state vector u;

w is the parameter representing the weights of the neural network $g_n$;

$u_0$ represents the state of the system at time t=0, being the initial position of the needle tip of each needle of the set of n needles.

9. The computer-implemented method according to claim 4, which further comprises defining a dynamic motion of each considered needle $E_i$, $i \in \{1, \ldots, n\}$, where $E_i$ represents a needle among a set of needles including n needles $E_1, \ldots, E_n$ according to a system of ordinary differential equations, where i=1, wherein a needle tip acceleration $\ddot{r}_i$ is a function of the initial position of the needle tip, its velocity $\dot{r}_i$, and the force $F_i$ applied to the needle tip in three directions of a coordinate system, $F_{i,x}$, $F_{i,y}$, $F_{i,z}$, resulting in:

$$\ddot{r}_i = f(F_i, \dot{r}_i, x_{i,0}, y_{i,0}, z_{i,0}),$$

$$\text{i.e.} \begin{cases} \ddot{x}_i = f_x(F_{i,x}, \dot{x}_i, x_{i,0}, y_{i,0}, z_{i,0}) \\ \ddot{y}_i = f_y(F_{i,y}, \dot{y}_i, x_{i,0}, y_{i,0}, z_{i,0}) \\ \ddot{z}_i = f_z(F_{i,z}, \dot{z}_i, x_{i,0}, y_{i,0}, z_{i,0}) \end{cases}$$

wherein the force F required to achieve an optimal trajectory for the tip of each needle tip of the set of n needles is learned through the neural network $g_n$ according to:

$$F = g_n(u, w),$$

$$\text{i.e.} \begin{pmatrix} F_{1,x}, F_{1,y}, F_{1,z} \\ \ldots \\ F_{n,x}, F_{n,y}, F_{n,z} \end{pmatrix} =$$

$$g_n(x_{1,0}, y_{1,0}, z_{1,0}, \ldots, x_{n,0}, y_{n,0}, z_{n,0}, TO_{position}, OAR_{position}, w)$$

wherein $TO_{position}$ is a position of the target object and $OAR_{position}$ is an optional parameter representing the position of the secondary biological body object.

10. The computer-implemented method according to claim 1, which further comprises using the obtained trajectories outputted within each plan as a guide for a clinician.

11. A system for automatically planning a minimally invasive thermal ablation, the system comprising:

an imaging system for acquiring images of a biological body including a target object to be ablated;

a memory for storing the acquired images and characterizing features of RF ablation needles usable for the thermal ablation;

a processing unit including a processor, said processing unit being configured for processing the acquired images;

said processing unit being configured for automatically carrying out the method according to claim 1; and a display for displaying the acquired images.

12. The system according to claim 11, which further comprises a projection system for projecting a trajectory determined for a needle of a final set on a display or on an external surface.

\* \* \* \* \*